United States Patent [19]
Rutz

[11] Patent Number: 5,121,986
[45] Date of Patent: Jun. 16, 1992

[54] METHOD AND APPARATUS FOR DETERMINING COMPOSITION OF FUEL MIXTURES

[75] Inventor: Mark D. Rutz, Hutchinson, Minn.

[73] Assignee: Atlantic Richfield Company, Los Angeles, Calif.

[21] Appl. No.: 510,656

[22] Filed: Apr. 17, 1990

[51] Int. Cl.$^5$ .............................................. G01N 21/41
[52] U.S. Cl. ...................................................... 356/133
[58] Field of Search .............................. 250/227, 301; 356/128-133

[56] References Cited

U.S. PATENT DOCUMENTS

| | | | |
|---|---|---|---|
| 4,770,129 | 9/1988 | Miyata et al. | 356/133 |
| 4,824,244 | 4/1989 | Miyata et al. | 356/133 |
| 4,834,533 | 5/1989 | Horike et al. | 356/133 |

FOREIGN PATENT DOCUMENTS

| | | | |
|---|---|---|---|
| 0049942 | 2/1989 | Japan | 356/133 |
| 0049943 | 2/1989 | Japan | 356/133 |

Primary Examiner—Richard A. Rosenberger
Assistant Examiner—Hoa Pham
Attorney, Agent, or Firm—Nilsson, Robbins, Dalgarn, Berliner, Carson & Wurst

[57] ABSTRACT

Apparatus and methods for determining the composition of a fuel mixture comprising hydrocarbons and oxygenates, wherein more than one measurement is made of the interaction of light passing through a light guide and the fuel mixture in which the light guide is immersed using light of a variety of different wavelengths and/or light guides having different indices of refraction. Data from the measurements is then interpreted to establish the concentration of hydrocarbons in the fuel mixture and/or the concentration and identity of the oxygenates. Pursuant to one type of embodiment of the invention, a plurality of light guides is provided, with particular light guides being used for each oxygenate to be analyzed (including water). In accordance with an alternative type of embodiment of the invention, a single light guide is employed with a single wide band light source and a plurality of light sensors.

21 Claims, 3 Drawing Sheets

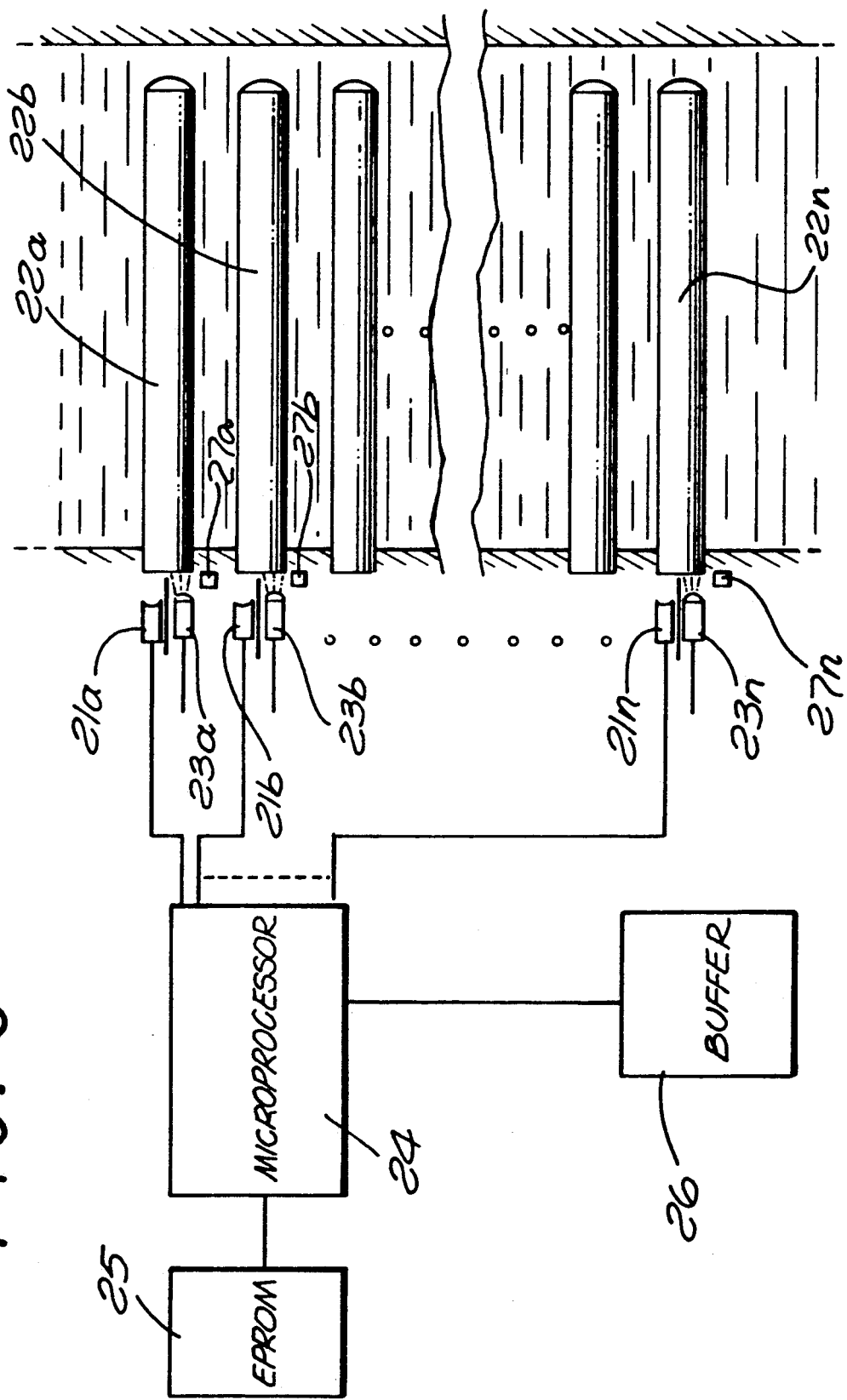

METHOD AND APPARATUS FOR DETERMINING COMPOSITION OF FUEL MIXTURES

BACKGROUND OF THE INVENTION

This invention relates to methods and apparatus for determining the concentration of various components, in particular oxygen (in the form of oxygen-containing compounds, or oxygenates), in hydrocarbon fuel mixtures containing, e.g., gasoline.

Considerable attention has been directed over the past several decades to the use of alcohol and alcohol/gasoline mixtures as fuel for automobiles. For example, retrofittable hardware has been developed to enable vehicles to run on pure alcohol or on an alcohol/gasoline mixture. Because adjustment of the carburetor and/or fuel warm up system is generally necessary to accommodate differences in fuel composition, there is a need for some type of monitor means able to determine accurately (and, preferably, on a substantially continuous basis) the alcohol and gasoline content of a mixture over the entire range of possible compositions (i.e., 100% alcohol to 100% gasoline).

In addition, it would be desirable to have some means for rapid and accurate determination of oxygenate quantity in gasolines for purposes of quality control and service station monitoring. Ideally, such a system would not only measure the dilution of gasoline with oxygenates, but also differentiate among the various oxygenate components (including, in particular, alcohols and water) and take into account variations in the composition of the hydrocarbon component.

Further, it would be advantageous to be able to determine accurately the fuel value of various gasoline compositions. A major portion of the fuel value of these compositions is derived from the aliphatic hydrocarbon (i.e., gasoline) components of the mixture. An accurate assessment of fuel value, however, would also take the amount of aromatic components of the mixture (e.g., benzene, toluene, xylenes, etc.) into account. Moreover, while many oxygenates have some fuel value, the heretofore available methods generally do not distinguish between such oxygenates and water, which has no fuel value.

Typically, finished gasoline is prepared from a variety of "blending stocks" which are combined to provide a product having the desired octane rating. Such blending stocks which are well known in the art include hydrocrackate, FCCU gasoline (regular unleaded), reformate (high octane unleaded), natural gasoline ("straight run"), coker gasoline and alkylate. Whereas hydrocrackates and alkylates are substantially free of aromatics, reformates may contain some aromatics and coker gasolines are generally rich in them. Normally, it is desirable to have a variety of stocks available for blending to provide a finished gasoline product, in view of synergies among the various types of stock with respect to octane rating; in general, the octane rating goes up with more complex mixtures. Such blending is an important aspect of the profitability of the operations of a refinery.

There have heretofore been disclosed systems for determining the alcohol/gasoline ratio in fuels by optical transducer means [van der Weide, J. et al., "A Retrofittable Alcohol/Petrol Carburation System," Paper B-25, 4th International Symposium on Alcohol Fuels, Brazil, pages 379-383 (1982)]. This type of system exploits differences between the refractive index of the liquid being evaluated and that of a permanent conductor (for example, a glass rod) inserted into the liquid.

Where the refractive index of the permanent conductor is different from that of the surrounding liquid medium, there will be a certain amount of reflection of light at the border surface of the two media. With a determination that a light source (for example, a light emitting diode or LED) has an essentially uniform intensity distribution over a particular aperture angle with respect to the permanent conductor, it can be readily calculated on the basis of optical principles that a portion of the light emitted within that aperture angle is reflected directly within the permanent conductor. This provides a stationary background independent of refractive index changes of the fuel mixture for a photoreceiver located at the opposite end of the permanent conductor from the light source. Another portion of the light is lost through direct transmission through the fuel mixture (also independent of the refractive index of the fuel mixture). The remaining portion of the light is reflected at the interface of the permanent conductor with the fuel mixture, and this reflection is dependent on the refractive index of the mixture.

According to the law of Snellius, the angle at which the light hitting the border surface of two media is still completely reflected is a function of the refractive indices of the two media. For example, van der Weide et al. describe evaluations of binary mixtures comprising ethanol (n=1.36) and gasoline (n=1.43). Using a glass rod (n=1.52) as a permanent conductor, van der Weide et al. calculated that a 100% ethanol composition would provide reflection up to a 27° angle of incidence at the interface between the permanent conductor and the liquid medium, whereas a 100% gasoline composition would reflect only up to a 20° angle. Using a round glass rod fitted at one end with a light emitting diode (650 nm) and a photoreceiver of the corresponding wavelength as a detector at the other, van der Weide et al. were able to confirm a correlation between the optical output voltage determined at the detector and the ethanol/gasoline ratio of the fuel mixture in which the central portion of the rod was immersed.

Unfortunately, the refractive indices of the liquids under consideration have a significant temperature sensitivity. Thus, over a temperature range of interest (e.g., −10° C. to +50° C.) the error in measurements obtained using the above-described system was unacceptably large (on the order of ±40%). Therefore, van der Weide et al. describe a further modification, wherein a second photoreceiver was fitted at the first end of the glass rod to monitor the amount of light transmission from the light source. A thermic connection between the two photoreceivers was made to achieve a thermic balance. As the light intensity registered by the second photoresistor depends on the temperature, the current was corrected for temperature over the range of −10° C. to +60° C.

Although such an arrangement does substantially reduce errors in the system based on variations in temperature, it has subsequently been determined by independent evaluation of data obtained in this manner using known compositions that such a system providing a single reading leads to calculations of fuel values with a margin of error on the order of ±10%. This is an unacceptably large margin, particularly in the context of supplying a suitable air/fuel ratio to, e.g., an internal combustion engine. For example, automobile engines have a fairly narrow range of air/fuel ratios at which they run acceptably; if the objective is optimizing the composition of vehicle emissions, the operating range is even narrower. This underscores the need for higher accuracy in the determination of fuel composition, particularly as more complex fuel mixtures are employed.

The devices for monitoring oxygenate levels in fuel compositions such as described above have heretofore been useful primarily to measure the degree of dilution of gasoline by oxygenates in general; in other words, a nominal gasoline concentration is obtained for the mixture. Such systems have a number of significant inherent drawbacks. For example, these devices sense water as if it were an oxygenated fuel; because water has no fuel value per se, the usefulness of such devices for making appropriate adjustments in fuel flow is limited with respect to fuels containing any significant water content.

Moreover, the known monitoring devices do not differentiate the various oxygenates with some fuel value from one another, and thus have utility primarily with respect to predetermined binary mixtures. Such differentiation among oxygenates is also of practical significance, as the materials available in the marketplace contain many different oxygenates and the required adjustments to fuel flow should be different for each oxygenate depending on its fuel value.

Finally, the various monitoring devices heretofore available do not make any adjustments for the varying aromatics content of fuels. As the commercially available fuels may vary significantly with respect to aromatics content, the ability to evaluate the amount of aromatics present in the fuel and to make corresponding adjustments in the calculated fuel value would be advantageous.

It is therefore an object of the present invention to provide an apparatus for determining the composition of a fuel mixture comprising gasoline and oxygenates with greater accuracy that has heretofore been possible. In particular, it is an object of the present invention to permit a rapid and accurate discrimination between oxygenates with no fuel value (e.g., water) and those with some fuel value, as well as to enable determination of the relative composition of the oxygenates component of the fuel mixture. In addition, it is a further object of the invention to provide methods and apparatus for determining the composition of fuel mixtures using low cost components which have low power consumption and which may conveniently be mounted in existing systems to enable fuel component stoichiometries to be determined in flexible fuel vehicles (e.g., automobiles and military vehicles) wherein such determinations of fuel composition would be of particular advantage, as well as in bulk fuel storage and transport facilities (for example, gasoline terminals and distribution systems).

SUMMARY OF THE INVENTION

In accordance with the present invention, there is provided apparatus and methods for determining the composition of a fuel mixture comprising hydrocarbons and oxygenates, wherein more than one measurement is made of the interaction of light passing through a light guide and the fuel mixture in which the light guide is immersed. To permit a more detailed analysis of the fuel composition, these measurements are preferably made using light of a variety of different wavelengths. Data from the measurements is then interpreted to establish the concentration of hydrocarbons in the fuel mixture and the concentration and identity of the oxygenates (including water). Analysis of the hydrocarbon concentration normally includes at least a determination of the content of aromatics; in preferred embodiments, there is a determination of paraffin, olefin and naphthene concentrations as well.

Pursuant to one type of embodiment of the invention, a plurality of light guides is provided, with particular light guides being used for each oxygenate to be analyzed (including water). The system determines the concentration of non-oxygenates in a manner similar to that disclosed in van der Weide et al. by interpretation of the interaction of a light beam of a first wavelength passing through a light guide immersed in the fuel mixture. Means for temperature correction as described in van der Weide et al. is suitably employed to determine as accurately as possible a nominal gasoline concentration for the fuel mixture. Further measurements using light of different wavelengths are carried out to determine the aromatics content of the gasoline component and to identify the proportion of the various oxygenates present in the mixture. In accordance with another type of embodiment of the invention, a single light guide is employed with a single wide band light source and a plurality of light sensors.

BRIEF DESCRIPTION OF THE DRAWINGS

FIG. 3 illustrates yet another embodiment of the monitor of the invention, in which a plurality of light guides each having a mirrored end is provided.

DETAILED DESCRIPTION OF THE INVENTION

Figure 1:
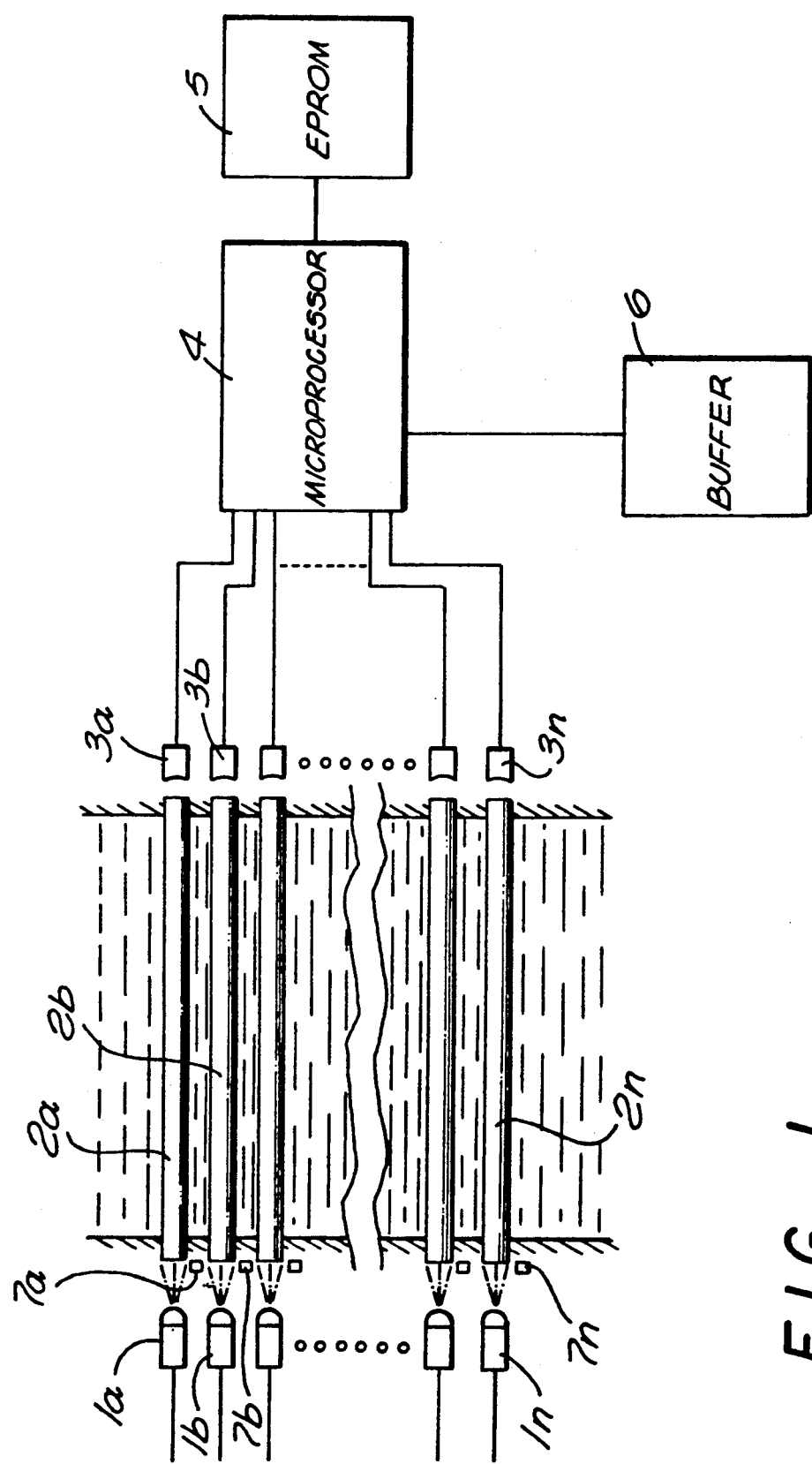
FIG. 1 illustrates a first embodiment of the monitor of the invention, comprising a plurality of discrete light guides.

In accordance with the present invention, the type of optical transducer arrangement disclosed, for example, by van der Weide et al. is employed not only to determine a nominal gasoline concentration, but also to permit determination of the absolute gasoline concentration and/or the identity and concentration of various oxygenates present in the mixture. These optical transducers exploit the distribution in refractive index of the various components of the fuel mixture. In general, a light guide having appropriate optical properties and inert to the fuel mixture with which it is in contact (suitably, a glass rod) is employed in combination with a light source (typically, an LED) and a light monitor (typically, a photocell). The ends of the transparent light guide are exposed to the atmosphere (but not stray light), while the midsection is immersed in the fuel mixture to be evaluated as to composition.

At one end, a light source of known wavelength generates a beam of light. A characteristic cone of light from this light source is completely reflected and transmitted the length of the light guide; the angle of this cone of light is related to the ratio of the index of refraction of the light guide to that of the liquid in which it is immersed. Depending on the refractive indices of the components of the liquid, up to a slightly larger angle the light is partly reflected and partly lost by transmission through the walls of the light guide; beyond the slightly larger angle, all light is lost to the surrounding liquid. In effect, the amount of light received by the photocell is a function of the composition of the liquid in which the light guide is immersed. Each component of the fuel mixture has a characteristic refractive index value, and thus will have a characteristic effect on the amount of light which is reflected or transmitted. This characteristic effect is regular for each component at a given wavelength with a given light guide and photocell system; it varies in intensity as the refractive index of the composition as a whole varies.

Pursuant to the method disclosed in van der Weide et al., in accordance with one embodiment of the invention a nominal gasoline concentration is determined based on a postulated refractive index of, e.g., $n=1.43$ for a premium (aliphatic hydrocarbon) fuel. It has been determined that a primary factor heretofore responsible for error in determining the hydrocarbon concentration of fuel mixtures has been variations in the aromatic content. In accordance with one aspect of the present invention, the absolute concentration of gasoline (i.e., the aliphatic non-oxygenated hydrocarbon component) is thus determined by adjusting the nominal gasoline concentration obtained in the manner known per se in the art to reflect the content of aromatics in the fuel mixture. Suitably, this adjustment is effected on the basis of measurements of the interaction of the fuel mixture (in particular, the aromatics content thereof) and a beam of light passing through a light guide.

In a preferred embodiment of the invention, at least a second wavelength of light selected so as to permit exploitation of the difference between the refractive indices of the aliphatic hydrocarbon components and the aromatics is employed to permit a determination of the aromatics concentration. Alternatively, the same wavelength of light used to determine nominal gasoline content is employed in conjunction with a different light guide having a suitably chosen index of refraction. Once the aromatic content is determined, the value calculated for the nominal hydrocarbon content (determined with reference to the oxygenates in a manner heretofore described in the prior art) may be adjusted so as to provide an absolute value for hydrocarbon content.

Whereas the nominal gasoline content is generally determined using a light source (such as a light emitting diode or LED) in the range from the near infrared to a wavelength of about 500 nanometers, measurement of the aromatics content is generally effected using a light source emitting at a wavelength on the order of about 10 to about 400 nm (as aromatics interact strongly with ultraviolet wavelengths). If a separate light guide of a composition different from that used for determining nominal gasoline concentration is employed for determination of aromatics, an additional photocell for temperature compensation may be necessary when the temperature sensitivity of the second light guide material is substantially different. While it is also possible to use the same wavelength of light with two or more such light guides of different compositions (and such an arrangement may be simpler and more economical), it is believed that the use of several different wavelengths carefully selected in conjunction with the refractive index of the optical element will provide optimal readings. Based on these determinations of the nominal gasoline concentration and the absolute aromatics concentration, the absolute gasoline concentration is readily determined by correction of the nominal gasoline (i.e., non-oxygenates) concentration to account for the aromatics.

In accordance with the present invention, a light guide having a different index of refraction and chosen with reference to the indices of refraction for the various commonly encountered aromatics may be employed to determine the aromatics concentration. The values for a number of such aromatics are reported in Table 1.

TABLE 1

| Refractive Index of Aromatics | |
|---|---|
| n-butylbenzene | 1.487 |
| isopropylbenzene | 1.489 |
| n-propylbenzene | 1.490 |
| sec-butylbenzene | 1.490 |
| t-butylbenzene | 1.490 |
| p-xylene | 1.493 |
| toluene | 1.494 |
| m-xylene | 1.495 |
| benzene | 1.498 |

Based on these values, a light guide of $n=1.45$ or less is suitable for use in determining the aromatic content of the fuel mixture. As a substantial correction for fuel values based on aromatics content may be made with sufficient accuracy without a determination of the identity and relative ratios of the various aromatic species, a single reading for aromatics content is normally sufficient. Determination of paraffin, olefin and/or naphthene content may be made in an analogous manner using an appropriate light guide for each component. In this manner, it is possible to provide a complete analysis of a hydrocarbon mixture's PONA (paraffin, olefin, naphthene, aromatics) content, from which a particularly accurate assessment of fuel value can be made.

Further in accordance with the present invention, the concentration of particular oxygenates in the fuel mixture may be determined. In accordance with a preferred embodiment of the invention, the concentrations of two or more oxygenates in the mixture are determined relatively, and the thus-obtained relative concentration values used to determine absolute concentrations based on the remainder indicated by determination of the gasoline (i.e., non-oxygenate) concentration of the fuel mixture. Pursuant to this mode of operation, there is the advantage that data to establish the absolute concentration of the various oxygenated species need not be collected. This avoids the difficulty of developing particular equipment (for example, specific sensors) suitable for generating such data. Once the gasoline concentration has been determined using the presently available devices (the suitability of which for such measurements has already been shown), it is only necessary to obtain relative concentration data for the various oxygenates in order to calculate absolute concentration values. Suitably, the relative concentrations of the various oxygenated species is also determined based on the interaction of one or more beams of light of suitable wavelengths with the fuel surrounding a light guide of particular optical characteristics.

The particular oxygenates present in the mixture may then be determined by difference or by linear combination using analogous refractive index techniques for each oxygenate. For example, a premium gasoline has a refractive index n of about 1.43; the concentration of such a gasoline in a mixture including alcohols is determined using an infrared beam transparent to the alcohols. By a strictly analogous procedure, the oxygenate composition of the mixture is similarly determined based on differences in refractive index among the oxygenates. Refractive index values for a number of commonly used oxygenates are indicated in Table 2.

TABLE 2

| Refractive Index of Oxygenates (sodium D line, 25° C.) | |
| --- | --- |
| methanol | 1.326 |
| water | 1.333 |
| ethanol | 1.359 |
| isopropyl ether | 1.367 |
| isopropanol | 1.375 |
| propyl ether | 1.379 |
| n-propanol | 1.383 |
| s-butanol | 1.395 |
| n-butanol | 1.397 |

In accordance with the present invention, the amount of a given oxygenate present in a mixture is determined using, e.g., a light guide of refractive index intermediate to that oxygenate and another component of the mixture (in particular, another oxygenate). Thus, to distinguish methanol from water, a light guide with $n=1.329$ (using the sodium D line) would be suitable; similarly, a light guide with $n=1.34$ enables distinction between water and ethanol. The oxygenate composition is determined similarly to the hydrocarbon composition using a system comprising a light source, temperature compensated light guide, and photocell. Using an appropriate algorithm, the microprocessor uses the voltage signals from the photocells to establish the composition of the fuel mixture.

As the molecular environment is unique for the oxygen in each oxygenate (including water), a corresponding unique spectral frequency can be used to advantage to optimize the sensitivity of the monitor to that particular oxygenate and thereby establish the relative concentration of the oxygenate in the mixture. In accordance with one preferred embodiment of the present invention, a separate unique light guide is employed for water and for each oxygenate carbon number.

In accordance with a further preferred embodiment of the invention, a microprocessor is employed to convert the collected data (in particular, photocell measurements of variances in intensity) into an analysis of the fuel composition. Such a system is capable of providing an output in any number of different forms for a variety of different uses in a manner known per se. For example, calculations of fuel value based on a determination of composition may be used to control the rate of fuel flow (e.g., to maintain an engine at a particular rate of operation). Alternatively, the composition may be monitored with respect to the content of water or any other component determined; the output in such a case may take the form of a determination that an upper and/or lower level for a given component or components has been reached.

Further in accordance with a preferred embodiment of the invention, calibration data may be continuously updated by online calibration using a standardized fuel mixture of known composition, so as to provide a table of evaluation data which is updated electronically. Such an arrangement permits calibration of the apparatus in the field using a standard of known composition to make appropriate adjustments of the monitor. It is preferred that the output be maintained separately from the monitor in a buffer. The buffer may then be suitably connected to input devices (e.g., for calibration) and to whatever type of output device (such as fuel flow signal, lights, meters, etc.) is desired in a given system. Using such a system, output results are available from the microprocessor continuously, with only a small computational lag.

With reference to FIG. 1, one general embodiment of the monitor device in accordance with the present invention comprises a plurality of discrete light source/light guide/photocell combinations. As illustrated, a plurality of light sources $1a, 1b \ldots 1n$ is provided, each of which is associated with a corresponding light guide $2a, 2b \ldots 2n$ and photocell $3a, 3b \ldots 3n$. Voltage values from each photocell are input into a microprocessor 4, which is associated with a suitable non-volatile electronically erasable programmable read only memory (EEPROM) 5 and a separate electronic buffer 6. The voltage signals are used by the microprocessor 4 with an appropriate algorithm to establish the composition of the fuel. This determination is then communicated to buffer 6 for further transmission external to the monitor. Through the use of an external device which may be attached to the buffer, the EEPROM 5 calibrations may be updated; for example, the monitor may be immersed in a fuel mixture of known composition and the composition entered through buffer 6. The microprocessor 4 could then be used to update the EEPROM 5. Through temperature compensation (in this embodiment, through the use of temperature compensating photocells $7a, 7b \ldots 7n$ associated with each light source), the algorithm for composition of the fuel mixture is generally simplified to a linear combination of the individually processed signals from each light guide; this avoids difficult correlational techniques which might be difficult to implement inexpensively with a microprocessor.

Figure 2:
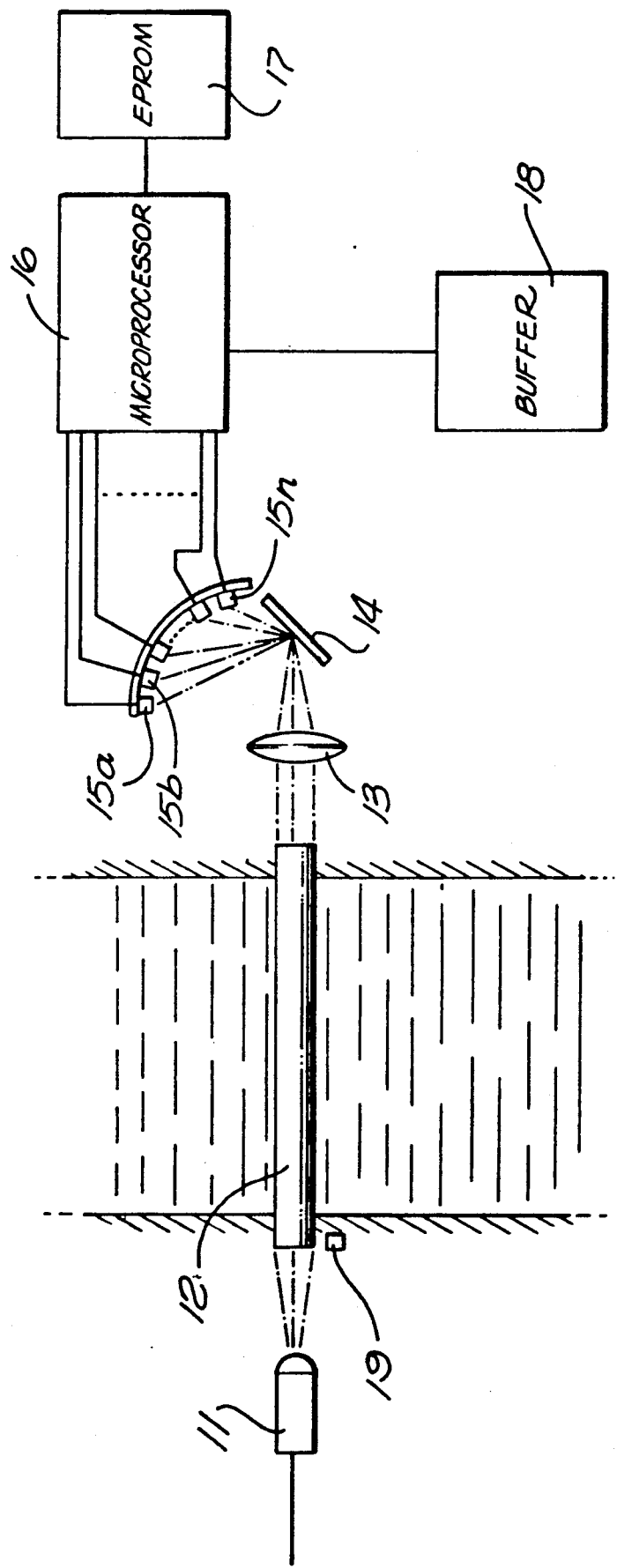
FIG. 2 illustrates another embodiment of the monitor of the invention, wherein a single light guide is employed.

FIG. 2 illustrates an alternative arrangement, wherein a single wideband light source 11 and light guide 12 are employed. The light source 11 covers the spectrum from ultraviolet to infrared. A focusing lens 13 and diffraction grating 14 are then employed so as to distribute the transmitted light by wavelength to a plurality of photocells $15a, 15b \ldots 15n$. Microprocessor 16, EEPROM 17, buffer 18 and temperature compensating photocell 19 are as in the previous embodiment.

As shown in FIG. 3, yet another alternative embodiment is provided which has the advantage that all of the electronics are placed on one side of the light guides. In this arrangement, a plurality of light sources $21a, 21b \ldots 21n$ are provided in combination with corresponding photocells $23a, 23b \ldots 23n$ at one end of a plurality of light guides $22a, 22b \ldots 22n$. Unlike the light guides of the previous embodiments, however, light guides 22 are mirrored at the opposite end; in this manner, the monitor is suitable for installation in existing pipe or tubing fittings without need for substantial alterations. Once again, microprocessor 24, EEPROM 25, buffer 26 and temperature compensating photocell 27 operate as in the previous embodiments.

For carrying out the measurement of multiple components in a mixture, there are a number of possible alternative strategies. Which approach is best for a given mixture in a given environment is typically determined through analysis and correlation of data developed using, e.g., mixtures of known composition including components present in the mixture of interest in the particular environment under consideration. It is generally appropriate to include one or more redundancies in measurement while evaluating a given approach, in order to reduce uncertainties to a useful level and to provide a basis for making assumptions about how to weight the relative measurements. The best strategy for evaluation of any given mixture in accordance with the present invention may thus be readily determined through routine optimization of the operating parameters for any systems and mixtures of interest. For example, relatively precise measurements of pure single components (e.g., water, methanol, ethanol, etc.) are possible, whereas one can obtain only less precise measurements of pool gasoline components, which are complex mixtures.

A particularly significant choice which must be made thus concerns which component or components would be measured absolutely in the first instance and which component(s) measured relatively. In the preceding discussion, the procedure as described for analysis of a typical fuel mixture involves measurement of the hydrocarbon portion absolutely, with adjustment for the aromatics content. The difference between dry, pure hydrocarbon gasoline and gasoline "diluted" with oxygenates is used to establish the proportion of oxygenates. Then, the oxygenates are measured relatively. By mapping the relative proportions of the oxygenates into the "plugged" oxygenates concentration, a fairly accurate analysis of the mixture is obtained for purposes of determining fuel value. As the oxygenates component of a typical fuel mixture may comprise a number of complex species which are difficult to identify and measure directly, the foregoing approach is often the most suitable manner in which to develop a reasonably accurate estimate of fuel value. With an absolute measurement of the hydrocarbon concentration including adjustment for at least the aromatics content (and, possibly, other non-oxygenate components of the mixture as well), then from precise relative measurements of the various oxygenates, an absolute estimate of the composition of the mixture is obtained with a minimum amount of instrumentation and optimum accuracy.

In all cases, the final determination of the composition of a mixture comprising n components requires $n-1$ measurements. For purposes of illustration, consider a mixture of water, methanol, ethanol and hydrocarbons (including aromatics). For such a mixture, four measurements would be necessary to determine the relative concentration of each of the three oxygenates and the aromatics content of the hydrocarbon component. With the components placed in order of increasing refractive index, the analysis of composition is suitably carried out using channels for measurement corresponding to a refractive index intermediate to each of the following: methanol and water; water and ethanol; ethanol and the hydrocarbon component; and the aromatics and the balance of the hydrocarbon component. By selecting device channels corresponding to refractive indices between each of the indicated components, the fuel is effectively divided into two portions by measurements on each channel.

Following a general analytical procedure as outlined above, a measurement on the channel corresponding to a refractive index intermediate to that of ethanol (the oxygenate having the highest index of refraction of the components listed) and the hydrocarbon component is used to determine the relative amounts of oxygenates and non-oxygenates present. This value for the non-oxygenates may in turn be adjusted to account for the aromatics content, using a channel corresponding to a higher refractive index (e.g., about 1.45). In this manner, the value obtained for the non-oxygenate component may be adjusted for aromatic content to provide an accurate assessment of its fuel value.

Once the relative oxygenate content as a whole has been determined, a series of additional measurements on channels corresponding to indices of refraction intermediate to those of the specific oxygenates are used to determine the relative proportion of each oxygenate present in the mixture. Thus, a measurement on the channel intermediate to methanol and water discriminates between methanol and the remaining components; similarly, the channel intermediate to water and ethanol "separates" the mixture into a portion comprising methanol and water on the one hand, and the remaining components on the other. Given the relative proportion of the three oxygenates already determined, the two additional measurements permit a determination of the amount of each oxygenate present in the mixture in a straightforward manner. For example, if the oxygenates content of a fuel mixture is determined to be 30%, determinations that the methanol content is 10% and the (methanol+water) content is 20% provide an analysis of the oxygenates as comprising one-third each of methanol, water, and ethanol. Other mixtures would be similarly ordered by refractive index and sensor/light guide arrangements chosen to provide the binary splits of the spectrum of possible mixture components appropriate for analysis of the composition; depending on the composition of these mixtures, alternative approaches (for example, absolute measurement of a predominant oxygenate with relative measurements of hydrocarbon constituents) may be employed. In turn, this information may then be used to provide a substantially accurate estimate of, e.g., gasoline octane rating or fuel heating value as desired for a given system, including periodically or even on a substantially continuous basis.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. A method for determining composition of a fuel mixture containing non-oxygenate and oxygenate components comprising:
   determining a concentration of said non-oxygenate component relative to said oxygenate component, thereby obtaining a nominal gasoline concentration for said fuel mixture;
   determining a concentration of aromatic materials relative to non-aromatic materials in said non-oxygenate component;
   adjusting said nominal gasoline concentration to reflect said aromatics concentration, thereby establishing an absolute gasoline concentration; and
   determining relative concentrations of materials comprising said oxygenate component, from which absolute concentrations of said materials are calculated.

2. Apparatus for determining the relative concentration of n components in a fuel mixture containing hydrocarbon and oxygenate components, said apparatus comprising:
   light source means for generating light of at least $n-1$ predetermined wavelengths, where n is an integer greater than 2;

photocell means for detecting intensity of said light at at least one location remote from said light source means;

said light source means operatively connected to said photocell means by at least one light guide means having a predetermined index of refraction, said light guide means immersible in the fuel mixture, to transmit said light from said light source means through the fuel mixture to said photocell means; and calculating means for determining concentrations of said n components based on said detected intensity.

3. Apparatus according to claim 2, wherein said light source means comprises a plurality of discrete light sources, each generating light of a predetermined wavelength.

4. Apparatus according to claim 3, wherein said light guide means comprises a plurality of discrete light guides, each light guide being associated with a particular light source.

5. Apparatus according to claim 2, wherein said light source means comprises a single wideband light source, said light guide means comprises a single light guide, and said apparatus further comprises means for separating transmitted light into a plurality of beams of different wavelengths.

6. Apparatus according to claim 2, wherein said hydrocarbon component contains aromatic and non-aromatic portions and wherein said n−1 wavelengths comprise a first wavelength for distinguishing between said oxygenate and said hydrocarbon components and a second wavelength for distinguishing between said aromatic and said non-aromatic portions of said hydrocarbon component.

7. Apparatus according to claim 2, wherein said oxygenate component contains at least two different oxygenate materials and wherein said n−1 wavelengths comprise a first wavelength for distinguishing between said oxygenate and said hydrocarbon components and at least a second wavelength for distinguishing between said different oxygenate materials.

8. Apparatus according to claim 2, wherein said calculating means comprises processor means for converting said detected intensities into calculated concentrations by reference to a table of corresponding intensity values obtained using a standardized fuel mixture of known composition.

9. Apparatus according to claim 8, further comprising calibration means for updating said table of corresponding intensity values.

10. Apparatus according to claim 2, further comprising temperature compensating photocell means for adjusting output of said light guide means to reflect variations in temperature.

11. Apparatus for determining the relative concentration of n components in a fuel mixture containing hydrocarbon and oxygenate components, said apparatus comprising:

light source means for generating light of at least one predetermined wavelength;

photocell means for detecting intensity of said light at at least one location remove rom said light source means;

said light source means operatively connected to said photocell means by n−1 light guide means, where n is an integer greater than 2 and where each light guide means has a preselected index of refraction associated with measurements at an index of refraction intermediate to the components of said mixture, said light guide means immersible in the fuel mixture, to transmit said light from said light source means through the fuel mixture to said photocell means; and calculating means for determining concentrations of said n components based on said detected intensity.

12. Apparatus for determining the relative concentration of n components in a fuel mixture containing hydrocarbon and oxygenate components, said apparatus comprising:

light source means for generating light of at least n−1 predetermined wavelengths;

photocell means for detecting intensity of said light at at least one location remote from said light source means;

said light source means operatively connected to said photocell means by n−1 light guide means, where each light guide means has a preselected index of refraction associated with measurements at an index of refraction intermediate to the components of said mixture, said light guide means immersible in the fuel mixture, to transmit said light from said light source means through the fuel mixture to said photocell means; and calculating means for determining concentrations of said n components based on said detected intensity, where n is an interger greater than 2.

13. Method for determining absolute hydrocarbon concentration of a fuel mixture containing aliphatic hydrocarbon, aromatic hydrocarbon and oxygenate components comprising the steps of measuring nominal concentration of the hydrocarbon component, by determining a first variation in intensity of light of a first wavelength passing through a light guide and correlating the first variation with values for refractive indices of the aliphatic hydrocarbon and oxygenate components, measuring the concentration of the aromatic hydrocarbon component, by determining a second variation in intensity of light of a second wavelength, differing from said first wavelength, passing through the light guide and correlating the second variation with a value for the refractive index of the aromatic component and then adjusting the measurement of the nominal concentration to provide an absolute value for the hydrocarbon content.

14. A method according to claim 13, wherein said concentration of the aromatic hydrocarbon component is determined by measuring variation in intensity of light of a wavelength of about 10 to about 400 nanometers.

15. A method according to claim 13, wherein said oxygenate component contains at least two different oxygenate materials, and wherein relative concentrations of said oxygenate materials are determined.

16. A method according to claim 15, wherein water content of said oxygenate component is determined.

17. A method according to claim 13, wherein said variations in intensity of light are measured with respect to transmission of light along at least one light guide, a portion of which is immersed in said fuel mixture.

18. Method for determining absolute hydrocarbon concentration of a fuel mixture containing aliphatic hydrocarbon, aromatic hydrocarbon and oxygenate components comprising the steps of measuring nominal concentration of the hydrocarbon component, by determining a first variation in intensity of light passing through a first light guide and correlating the first variation with values for refractive indices of the aliphatic hydrocarbon and oxygenate components, measuring the concentration of the aromatic hydrocarbon component, by determining a second variation in intensity of the light, passing through a second light guide, having a refractive index which differs from the first, and correlating the second variation with a value for the refractive index of the aromatic component and then adjusting the measurement of the nominal concentration to provide an absolute value for the hydrocarbon content.

19. A method according to claim 18, wherein relative concentrations of said aliphatic hydrocarbon and aromatic components are determined using a light guide having an index of refraction of 1.45 or less.

20. A method according to claim 18, wherein relative concentration of water and methanol in said oxygenate component is determined using a light guide having an index of refraction of 1.329.

21. A method according to claim 18, wherein relative concentration of water and ethanol in said oxygenate component is determined using a light guide having an index of refraction of 1.34.

* * * * *

UNITED STATES PATENT AND TRADEMARK OFFICE
CERTIFICATE OF CORRECTION

PATENT NO. : 5,121,986
DATED : June 16, 1992
INVENTOR(S) : Mark D. Rutz

It is certified that error appears in the above-identified patent and that said Letters Patent is hereby corrected as shown below:

In column 11, line 62, "remove rom" should read - - - remote from - - -

Signed and Sealed this

Twenty-first Day of September, 1993

Attest:

BRUCE LEHMAN

Attesting Officer

Commissioner of Patents and Trademarks